(12) United States Patent
Mendiratta et al.

(10) Patent No.: US 7,923,220 B2
(45) Date of Patent: Apr. 12, 2011

(54) PROCESS FOR PREPARING HIGH LEVELS OF INTERFERON BETA

(75) Inventors: Sanjeev Kumar Mendiratta, Gujarat (IN); Vibhor Saraswat, Gujarat (IN); Dharmedra Chudasama, Gujarat (IN)

(73) Assignee: Cadila Healthcare Limited, Gujarat (IN)

( * ) Notice: Subject to any disclaimer, the term of this patent is extended or adjusted under 35 U.S.C. 154(b) by 562 days.

(21) Appl. No.: 11/793,114

(22) PCT Filed: Dec. 19, 2005

(86) PCT No.: PCT/IN2005/000419
§ 371 (c)(1),
(2), (4) Date: Apr. 7, 2008

(87) PCT Pub. No.: WO2006/067804
PCT Pub. Date: Jun. 29, 2006

(65) Prior Publication Data
US 2009/0215121 A1    Aug. 27, 2009

(30) Foreign Application Priority Data

Dec. 20, 2004  (IN) .......................... 1370/MUM/2004

(51) Int. Cl.
*C12P 21/00*    (2006.01)
(52) U.S. Cl. .................................... 435/69.51; 435/71.2
(58) Field of Classification Search ........................ None
See application file for complete search history.

(56) References Cited

U.S. PATENT DOCUMENTS

| | | | | |
|---|---|---|---|---|
| 4,656,132 A | * | 4/1987 | Ben-Bassat et al. | 435/69.5 |
| 4,746,608 A | * | 5/1988 | Mizukami et al. | 435/69.51 |
| 5,462,860 A | * | 10/1995 | Mach | 435/34 |

* cited by examiner

*Primary Examiner* — Robert Landsman
*Assistant Examiner* — Bruce D Hissong
(74) *Attorney, Agent, or Firm* — Ladas & Parry LLP

(57) ABSTRACT

The present invention relates to a novel process for the production of interferon-beta in improved yields by fermentation.

13 Claims, 5 Drawing Sheets

SEQUENCE ID 1:

```
Met Ser Tyr Asn Leu Leu Gly Phe Leu Gln Arg Ser Ser Asn Phe Gln
 1           5              10             15

Cys Gln Lys Leu Leu Trp Gln Leu Asn Gly Arg Leu Glu Tyr Cys Leu
         20              25          30

Lys Asp Arg Met Asn Phe Asp Ile Pro Glu Glu Ile Lys Gln Leu Gln
         35              40          45

Gln Phe Gln Lys Glu Asp Ala Ala Leu Thr Ile Tyr Glu Met Leu Gln
         50              55          60

Asn Ile Phe Ala Leu Phe Arg Gln Asp Ser Ser Thr Gly Trp Asn
         65              70          75          80

Glu Thr Ile Val Glu Asn Leu Leu Ala Asn Val Tyr His Gln Ile Asn
             85              90          95

His Leu Lys Thr Val Leu Glu Glu Lys Leu Glu Lys Glu Asp Phe Thr
            100             105         110

Arg Gly Lys Leu Met Ser Ser Leu His His Lys Arg Tyr Tyr Gly Arg
            115             120         125

Ile Leu His Tyr Leu Lys Ala Lys Glu Tyr Ser His Cys Ala Trp Thr
            130             135         140

Ile Val Arg Val Glu Ile Leu Arg Asn Phe Tyr Phe Ile Asn Arg Leu
            145             150         155         160

Thr Gly Tyr Leu Arg Asn
                165
```

FIGURE 5

SEQUENCE LISTING

<160> NUMBER OF SEQ ID NOS: 1

<210> SEQ ID NO 1
<211> LENGTH: 166
<212> TYPE: PRT
<213> ORGANISM: Escherichia coli

<400> SEQUENCE: 1

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Leu Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

PROCESS FOR PREPARING HIGH LEVELS OF INTERFERON BETA

FIELD OF INVENTION

The present invention relates to a novel process for the production of interferon-beta in improved yields by fermentation.

BACKGROUND OF THE INVENTION

Three major types of interferons have been identified in humans: alpha-, beta-, and gamma-interferons. These are produced by a variety of cells upon exposure to viruses, mitogens, polynucleotides etc. They possess anti-viral, anti-proliferative and immunomodulatory properties. IFN-β is used as an effective treatment for multiple sclerosis [Corboy J R. et al., *Current Treatment Options in Neurology*, 5, 35-54 (2003)], hepatitis B and hepatitis C.

Betaseron, an analogue of human IFN-β where serine was genetically engineered to substitute for cysteine at position 17, is known as IFN-β 1b (U.S. Pat. No. 4,588,585). The molecule is a small polypeptide of 165 amino acids with a single disulphide bond, and is produced as a non-glycosylated protein. The glycosylated variant of IFN-β, known as IFN-β 1a, has a carbohydrate chain at position 80 and is expressed in Chinese Hamster Ovary cells [Conradt et al., *J. Biol. Chem.*, 262, 14600-5 (1987); Kagawa et al., *J. Biol. Chem.*, 263, 17508-15 (1988); Oh et. al., *Biotechnol. Prog.*, 21, 1154-64 (2005); U.S. Pat. No. 5,795,779 (McCormik et al); U.S. Pat. No. 5,554,513 (Revel et al)].

IFN-β was initially produced by inducing the leukocytes by treating them with viruses. But the therapeutic use of interferon-β produced in this manner is questionable because of the high chances of the presence of various contaminants (e.g. viruses) in such preparations. Recombinant technology has made it possible to produce IFN-β, which is free from viral contamination. Native IFN-β is a glycoprotein, and its production has been reported in mammalian, insect and yeast cells, as described in Mantei et al., *Nature* 297: 128 (1982); Ohno et al., *Nucl Acid. Res.* 10: 967 (1982); and Smith et al., *Mol. Cell. Biol.* 3: 2156 (1983), respectively.

U.S. Pat. No. 5,795,779 (McCormick et al.) discloses high level production of IFN-β from recombinant CHO cells. U.S. Pat. No. 5,554,513 (Revel et al.) discloses two subtypes of IFN-β and describes methods to produce it in CHO cells. But a!! commercial animal cell culture processes are associated with technical difficulties like, longer process time, requirement for maintaining stringent culturing conditions, high cost of culture media etc.

Also, the glycosylation was shown to play no role in the biological activity of the protein [Taniguchi, et al., *Gene* 10, 11-15 (1980); E. Knight Jr., *Proc. Natl Acad. Sci.*, 73, 520 (1976); E. Knight Jr. and D. Fahey, *J. Interferon Res.* 2(3), 421 (1982)] thereby underscoring the advantage of carrying out the production in the commonly used host, *E. coli*. Various recombinant proteins have been produced in *E. coli* by this technology [Saraswat et al. FEMS Microbiology Lett., 179, 367-73 (1999); Holowachuk & Ruhoff, Protein Expr. Purif. 6, 588-96 (1995); Kim et. al, Biotechnol. & Bioeng., 69, (2000); Kim et al., Bioprocess and Biosystems Engineering, 24 (2001); Saraswat et. al. Biotechnol. Lett., 22, 261-5 (2000); Lee et. al., FEMS Microbiology Lett., 195, 127-132 (2001); Saraswat et. al. Biochemistry, 41, 15566-77 (2002); Wang et al., Chin. J. Biotechnol. 11, 45-81 (1995)].

IFN-β has been cloned and expressed in *E. coli* (Taniguchi, et al., *Gene* 10, 11-15 (1980).

EP 0048970 (Goeddel et al.) describes microbial production of mature human fibroblast interferon.

Like for any therapeutic protein, it is desirable to obtain high levels of interferon-β for commercial purposes. EP 0036776 (Kield et al.) discloses novel vectors based on tryptophan promoter-operator system for the efficient production of heterologous protein in bacteria. U.S. Pat. No. 4,686,191 (Itoh et al.) discloses methods to obtain efficient expression of interferon-β in *E. coli*, by using improved vectors with trp promoter, to increase the efficiency of protein synthesis. U.S. Pat. No. 4,499,188 (Konrad et al.) claims to solve the problem of monitoring repressor levels during culturing, when trp promoter is used for interferon-β production. Mizukami et al. in U.S. Pat. No. 4,746,608 suggest the method of culturing the recombinant microorganism at a temperature 10 to 25° C. lower than the optimum growth temperature, for obtaining a high yield of interferon-β. Ben-Bassat et al. in U.S. Pat. No. 4,656,132 claim to solve the problem of lower yields of interferon-β by addition of an effective amount of a water-soluble alkanol of 1 to 4 carbon atoms and/or a mixture of amino acids that supports bacterial growth during the late phase of the cultivation. Cousens et al. in U.S. Pat. No. 5,866,362 have suggested the production of interferon-β as protein aggregates by growing the host cells in a medium comprising an effective amount of $Cu^{++}$ so that they form inclusion bodies in the host cell from which the protein is isolated and purified. But none of the processes could achieve satisfactory levels of interferon-β. Because of the hydrophobic nature of interferon-β, the synthesized protein interferes with cell growth and thus the production of interferon-β is not achieved at significantly high levels.

Dorin et al. in U.S. Pat. No. 5,814,485 disclose certain conditions that increase the expression of hydrophobic polypeptide like interferon-β in transformed host cells. The critical conditions for the invention (U.S. Pat. No. 5,814,485) arc Potassium ion concentration no greater than 120 mM and/or Sodium ion concentration no greater than 40 mM and/or p11 between 4.8 and 6.8 during the induction of protein production.

The present invention discloses similar to higher level of production of interferon-β as that disclosed in U.S. Pat. No. 5,814,485 by inducing the protein production at conditions, which are not dependent on maintaining low levels of Potassium and Sodium ion concentrations in the production media. This is achieved by careful selection of the nitrogen source and other nutrients/additives before or during the production phase.

SUMMARY OF INVENTION

In one aspect, the present invention provides a method to produce recombinant interferon-β in high levels using selective culture conditions.

In another aspect, the present invention provides high levels of interferon-β even under levels of $K^+$, and $Na^+$ ion concentration that are higher than that dictated in the prior art, by careful selection of nitrogen source and other nutrients in the production and/or pre-production medium.

In one of its aspects the present invention provides high levels of interferon-β even under higher pH than that dictated in the prior art for obtaining high yield of interferon beta.

In yet another aspect the present invention obtains significantly high levels of IFN-β using a process of fermentation in which culturing conditions are more cost effective than prior art processes.

BRIEF DESCRIPTION OF DRAWINGS

FIG. 5 shows the amino acid sequence of IFN-β (Seq ID 1)

DESCRIPTION OF THE INVENTION

Figure 1:
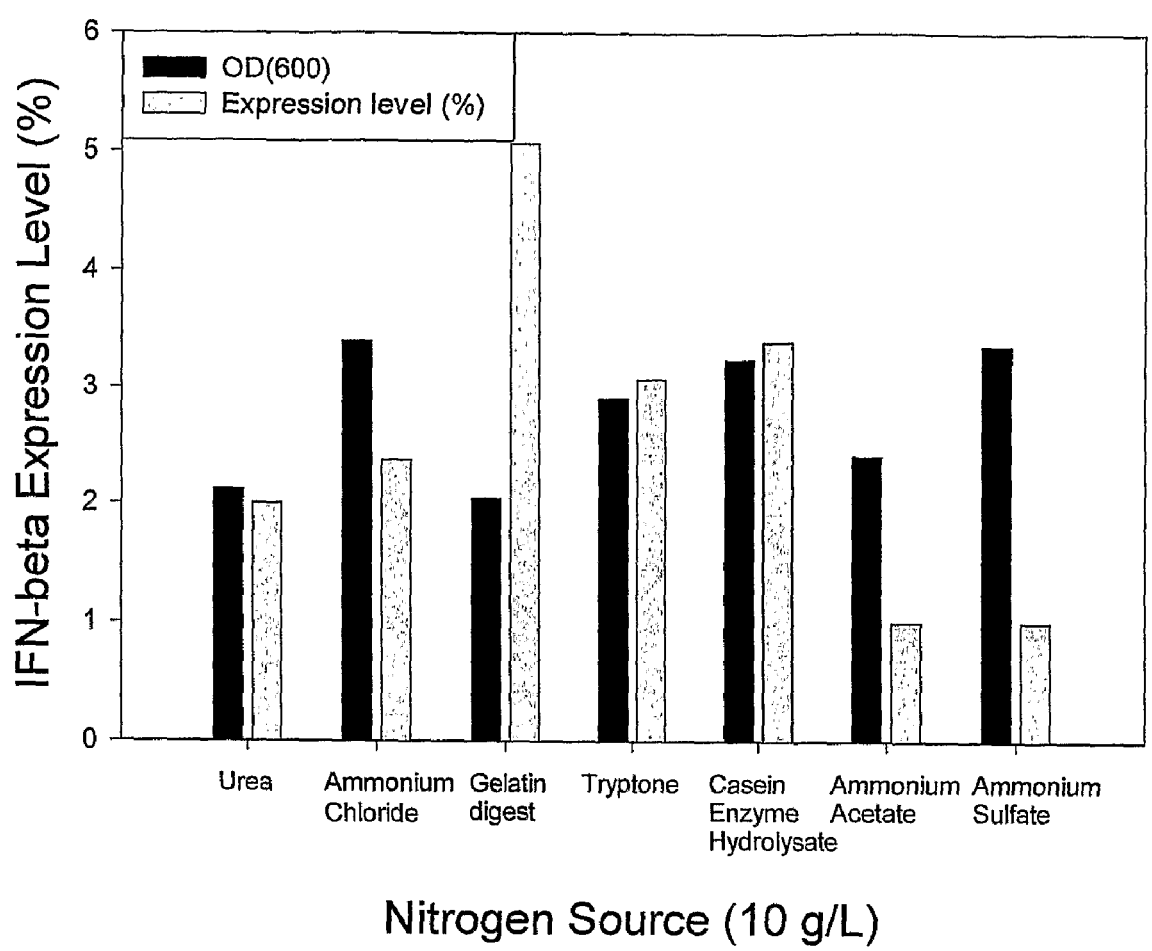
FIG. 1 shows the effect of various nitrogen sources on IFN-β expression level. Experiments conducted in shake-flasks. Wherein the Grey bars indicate the expression levels obtained with complex and inorganic nitrogen sources, namely Ammonium acetate, Ammonium chloride, Ammonium sulfate, Casein Enzyme Hydrolysate, Gelatin digest, Tryptone, and Urea (10 g/L at the time of addition of inducer), and Black bars indicate the optical density (at 600 nm) at the corresponding time point. All values obtained from 8-h post-induction samples.

The present invention relates to a novel fermentation process for the production of interferon-β at high levels of expression. Various culturing conditions for the high level production of interferon-β protein using transformed *Escherichia coli* have been studied leading to an alternate, highly efficient process for its production. The present invention discloses culturing conditions for improved product yields. The present invention is described in detail below:

Any interferon-β (also referred here as 'IFN-β') polypeptide can be utilized. The term "interferon-β" or "IFN-β" refers to native IFN-β, muteins, fragments, fusions, analogs and derivatives thereof, either exhibiting at least 60% biological or receptor binding activity as the native IFN-β, or retaining at least about 80% amino acid identity with SEQ ID No. 1 (amino acid sequence of human IFN-β).

The IFN-β gene used in the present invention is the mutated form of the native gene where the 17$^{th}$ amino acid, serine, was genetically engineered to substitute for cysteine according to U.S. Pat. No. 4,588,585. This mutated analogue of human IFN-β is known as IFN-β 1b. The source of the native IFN beta gene used in the present invention is human lung fibroblast cell line, MRC 5, from NCCS, Pune, INDIA. The above described mutation was introduced into this gene using standard molecular biology techniques reported in the prior art.

Suitable host cells, preferably *Escherichia coli* are transformed with a suitable expression vector comprising the coding sequence of IFN-β and a suitable promotor selected from t7, tac, and similar promoters along with other vector components using transformation techniques well known in art. The *Escherichia* strain for the present invention is selected from the group comprising *Escherichia coli* BL21(DE3) and its derivatives. Preferably the host is *Escherichia coli* BL21 (DE3) which is deposited at ATCC deposit no ATCC 47092. The source of the *Escherichia coli* BL21(DE3) used in the present invention is Stratagene, USA.

The transformed host cells were initially cultured under conditions for growth in batch mode of fermentation. The culture media used in the process of the present invention comprise carbon and energy sources selected from the group comprising of glucose, glycerol, fructose, maltose, galactose and the like or mixtures thereof, nitrogen source selected from the group comprising of yeast extract, tryptone, peptone, casein enzyme hydrolysate, soyabean casein hydrolysate, gelatin, and the like or mixtures thereof, suitable salts/nutrients selected from the group consisting of citric acid, potassium chloride, sodium chloride, magnesium sulphate, di-ammonium hydrogen phosphate, potassium dihydrogen phosphate, sodium butyrate, thiamine, glycine, and zinc chloride. The pH is maintained at about 5-8. The temperature is maintained at about 30-40° C. Other fermentation conditions like aeration and agitation, inoculum, time of inoculation etc. chosen as per convenience of a person skilled in the art.

Substrate limiting fed-batch mode of fermentation is initiated once the substrate concentration in the culture media is maintained at about 0.5 g/L or less. After achieving a cell density of 1-30 g/L dry cell weight and a glucose concentration less than 0.5 g/L, addition of the pre-production medium was done. The pre-production medium comprise, a nitrogen source selected from the group comprising complex nitrogen sources like tryptone, casein enzyme hydrolysate (CEH), soyabean casein hydrolysate, gelatin digest, and the like, their combinations with each other and their combinations with yeast extract, suitable salts/nutrients selected from the group comprising of citric acid, potassium chloride, sodium chloride, magnesium sulphate, di-ammonium hydrogen phosphate, potassium dihydrogen phosphate, sodium butyrate, thiamine, glycine, and zinc chloride, suitable antibiotics like Ampicillin, Kanamycin etc., which are selected as required by the process. The pH is maintained at about 6.3-8, preferably at pH 6.5-7.0, and the temperature is maintained at about 25-40° C., preferably at about 37° C. The total K$^+$ concentration of the culture media is greater than 120 mM and the Na$^+$ concentration is greater than 40 mM, preferably in the range of 60-80 mM. Carbon source may not be added to the pre-production medium. Induction of protein production is done after the addition of the pre-production medium. A suitable inducer can be added in a single lot, multiple lots or in a continuous manner. A continuous feed of production medium (in fed-batch mode) is started immediately after adding the inducer. The production medium comprises a carbon source in addition to the constituents of the pre-production medium. Suitable carbon source can be selected from the group comprising of glycerol, glucose, fructose, maltose, galactose and the like or mixtures thereof. The preferred carbon source of the present invention is glucose. The pH of the medium is maintained at about 6.3-8, preferably at pH 6.5-7.0, and the temperature is maintained at about 25-40° C., preferably at about 37° C. All other conditions of fermentation are selected as known in the prior art. Throughout the production phase of fermentation the total K$^+$ concentration of the culture media is greater than 120 mM and the Na$^+$ concentration is greater than 40 mM. After 5 to 24 hours, the culture medium is removed and subjected to downstream processing according to the techniques described in art. The process of the present invention results in the production of the hydrophobic proteins like IFN-β in high yields (expression level in the range of 4-28% of the total cellular protein) as estimated densitometrically using protein bands obtained with SDS-PAGE method.

The examples below further describe the invention. These examples are provided as illustrations and should not be construed as limiting the invention in any way.

Example 1

Expression of IFN Beta in Media Comprising Casein Enzyme Hydrolysate. Sodium and Thiamine The culture of *E. coli* BL21 (DE3) cells transformed with the IFN-beta gene was grown in Luria-Bertini medium (pH 7.0) with Ampicillin (100 mg/L) for 14 hours at 37° C. and 200 rpm in an incubator shaker. Subsequently the biomass was aseptically removed by centrifugation at 7135×g for 15 minutes at 20° C. and aseptically re-suspended in the production medium. The composition of the media used for the production of IFN-β was as follows:

| Component | Concentration at the time of induction |
|---|---|
| Glucose | 5 g/L |
| Casein Enzyme Hydrolysate | 20 g/L |
| Sodium cation | 60 mM |
| Potassium cation | 90 mM |
| Thiamine | 7 g/L |
| Ampicillin | 100 mg/L |

The IFN-β gene was subsequently induced by adding filter-sterilized IPTG (2 mM) at 37° C. The temperature during the production phase was kept at 37° C. and the pH was in the range of 5.3-7.2. Every two hours samples were taken and pH was adjusted to about 7.0. IFN-beta expression level in 8-h post-induction sample was 10.49% as measured densitometically using protein bands obtained with SDS-PAGE.

Example 2

Expression of IFN Beta in Media Comprising Tryptone, Sodium and Thiamine

The experiment was performed in the same manner as that reported in Example 1 except with Tryptone as the nitrogen source in the production media having the following composition:

| Component | Concentration at the time of induction |
|---|---|
| Glucose | 5 g/L |
| Tryptone | 20 g/L |
| Sodium cation | 60 mM |
| Potassium cation | 90 mM |
| Thiamine | 7 g/L |
| Ampicillin | 100 mg/L |

The IFN-β gene was subsequently induced by adding filter-sterilized IPTG (2 mM) at 37° C. The temperature during the production phase was kept at 37° C. and the pH was in the range of 5.3-7.2. Every two hours samples were taken and pH was adjusted to ~7.0. IFN-beta expression level in 8-h post-induction sample was 7.15%.

Example 3

Effect of Various Nitrogen Sources on Expression Level at Shake Flask Level

The culture of *E. coli* BL21 (DE3) cells transformed with the IFN-beta gene was grown in Luria-Bertini medium (pH 7.0) with Ampicillin (100 mg/L) for 14 hours at 37° C. and 200 rpm in an incubator shaker. Subsequently the biomass was aseptically removed by centrifugation at 7135×g for 15 minutes at 20° C. and aseptically re-suspended in the production medium. The composition of the media used for the production of IFN-β was as follows:

| Component | Concentration at the time of induction |
|---|---|
| Glucose | 5 g/L |
| Nitrogen source | 10 g/L |
| Potassium Cation | 90 mM |
| Ampicillin | 100 mg/L |

The nitrogen sources used in the experiment were Ammonium acetate, Ammonium chloride, Ammonium sulfate, Casein Enzyme Hydrolysate, Gelatin digest, Tryptone, and Urea. The IFN-β gene was subsequently induced by adding filter-sterilized IPTG (2 mM) at 37° C. The temperature during the production phase was kept at 37° C. and the pH was in the range of 5.3-7.2. Every two hours samples were taken and pH was adjusted to ~7.0. IFN-beta expression levels in 8-h post-induction sample are shown in FIG. 1.

Example 4

Concentration Dependence of Nitrogen Sources on Expression Level

Figure 2:
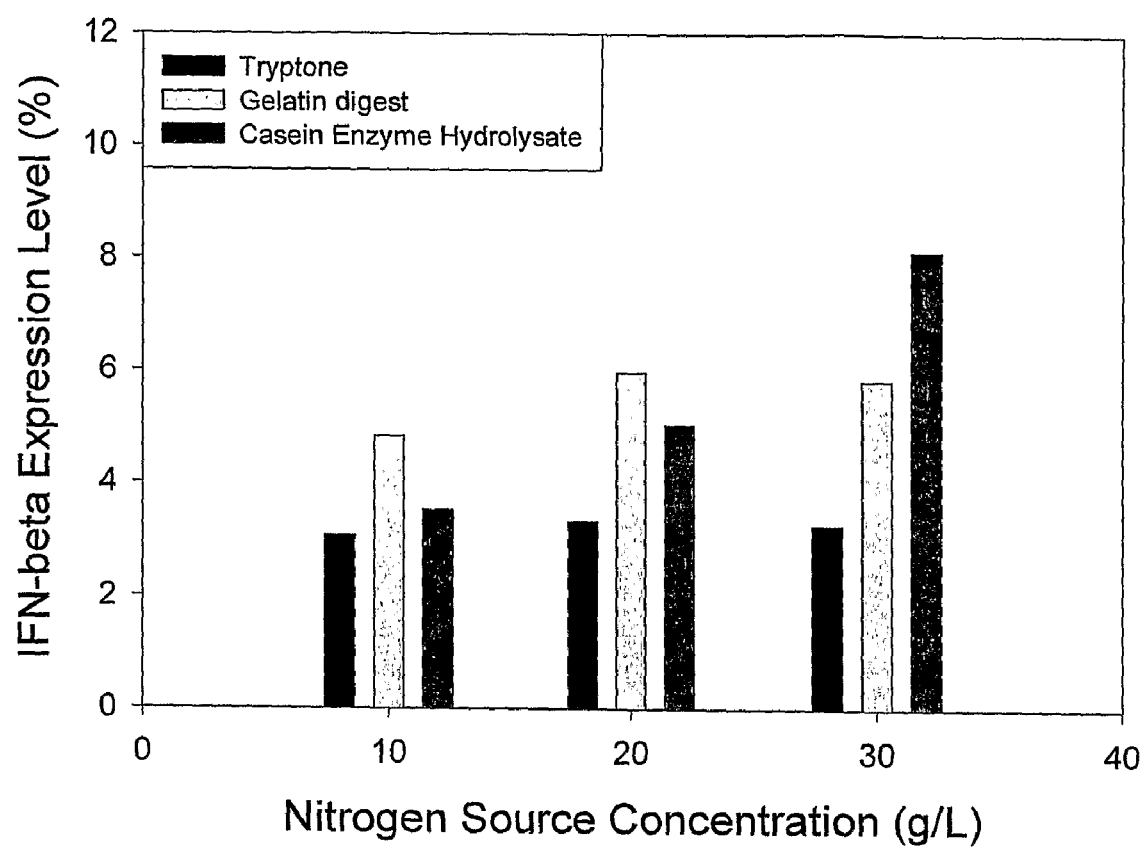
FIG. 2 shows the effect of various concentrations of the selected nitrogen sources on IFN-β expression level. Experiments conducted in shake-flasks. Wherein the expression levels shown with different concentrations (10, 20 and 30 g/L, at time of the addition of IPTG) of complex nitrogen sources: Casein Enzyme Hydrolysate (Dark Gray bars), Gelatin digest (Light Gray bars), and Tryptone (Black bars).

The effect of different concentration of nitrogen sources on the production of interferon beta production was tested (FIG. 2). All other parameters were the same as that used for Example 1, except Na$^+$ and Thiamine concentrations, which were not tested here. The composition of the media used for the production of IFN-β was as follows:

| Component | Concentration at the time of induction |
|---|---|
| Glucose | 5 g/L |
| Nitrogen Source | 10-30 g/L |
| Sodium cation | 60 mM |
| Potassium cation | 90 mM |
| Thiamine | 7 g/L |
| Ampicillin | 100 mg/L |

The IFN-β gene was subsequently induced by adding filter-sterilized IPTG (2 mM) at 37° C. The temperature during the production phase was kept at 37° C. and the pH was in the range of 5.3-7.2. Every two hours samples were taken and pH was adjusted to about 7.0.

The results of IFN-beta expression level in 8-h post-induction samples are summarized in Table 1.

TABLE 1

| Nitrogen Source | Concentration (g/L) | IFN beta Expression Level (%) |
|---|---|---|
| Gelatin digest | 10 | 4.83 |
|  | 20 | 5.96 |
|  | 30 | 5.81 |
| Tryptone | 10 | 3.07 |
|  | 20 | 3.32 |
|  | 30 | 3.25 |

TABLE 1-continued

| Nitrogen Source | Concentration (g/L) | IFN beta Expression Level (%) |
|---|---|---|
| Casein Enzyme Hydrolysate | 10 | 3.25 |
|  | 20 | 5.02 |
|  | 30 | 8.10 |

Example 5

Effect of Tryptone on IFN Beta Expression Level

A seed culture of *E. coli* BL21 (DE3) cells transformed with the IFN-beta gene was inoculated in the growth media of the following composition.

| Component | Concentration before inoculation |
|---|---|
| $KH_2PO_4$ | 13.3 g/L |
| $(NH_4)_2HPO_4$ | 4.0 g/L |
| Yeast extract | 1.0 g/L |
| Glucose | 10.0 g/L |
| Citric acid | 1.7 g/L |
| $MgSO_4 \cdot 7H_2O$ | 1.2 g/L |
| Trace element solution | 20.0 mL/L |
| Ampicillin | 100 mg/L |

Trace metal solution:

| Component | Concentration |
|---|---|
| $FeCl_3 \cdot 6H_2O$ | 0.162 g/L |
| $ZnCl_2 \cdot 4H_2O$ | 0.0144 g/L |
| $CoCl_2 \cdot 6H_2O$ | 0.12 g/L |
| $Na_2MoO_4 \cdot 2H_2O$ | 0.012 g/L |
| $CaCl_2 \cdot 2H_2O$ | 0.006 g/L |
| $CuCl_2$ | 1.9 g/L |
| $H_3BO_3$ | 0.5 g/L |

Adding the following media in substrate limited fed-batch mode brought about the major increase in biomass:

| Component | Concentration |
|---|---|
| Glucose | 700 g/L |
| $MgSO_4 \cdot 7H_2O$ | 20 g/L |
| Trace element solution | 20 mL/L |
| Ampicillin | 1.5 g/L |

In growth phase ammonium hydroxide was used as the pH regulator to maintain the pH in the range of 6.8 to 7.0. The temperature was maintained at 37° C. After achieving optical density of about 50 AU (at 600 nm), pre-production media was added to get the following concentrations of the individual components of the said media in the culture broth:

| Component | Concentration |
|---|---|
| Tryptone | 10 g/L |
| Potassium cation | 90 mM |

The expression of IFN beta gene was induced by aseptically adding a filter-sterilized solution of IPTG (2 mM) to the culture broth. The following production media was subsequently added to increase the expression level of IFN-beta:

| Component | Concentration |
|---|---|
| Glucose | 270 g/L |
| $MgSO_4 \cdot 7H_2O$ | 1 g/L |
| Tryptone | 20 g/L |
| Potassium cation | 90 mM |
| Ampicillin | 1 g/L |

In production phase ammonium hydroxide was used as the pH regulator to maintain the pH 7.0. The temperature was maintained at 37° C. The expression level of IFN beta, as determined by SDS-PAGE, was 15.24% in the 12-h post-induction sample.

Example 6

Effect of Casein Enzyme Hydrolysate on IFN beta Expression Level

The experiment was performed in the similar manner as Example 5, except that instead of using Tryptone, Casein Enzyme Hydrolysate was used as the chief nitrogen source in Example 6. The final concentrations of Casein Enzyme Hydrolysate were 10 g/L and 20 g/L, in pre-induction and production media, respectively. The expression level of IFN beta, as determined by SDS-PAGE, was 24.76% in the 12-h post-induction sample.

Example 7

Effect of a Combination of Tryptone and Yeast Extract on IFN Beta Expression Level The experiment was performed in the similar manner as Example 5, except that instead of using Casein Enzyme Hydrolysate, a combination of Tryptone and Yeast Extract was used as the chief nitrogen source in Example 7. The final concentrations of Tryptone and Yeast Extract in culture broth after the addition of pre-induction medium were 10 g/L and 5 g/L, respectively. The concentrations of Tryptone and Yeast Extract in production medium were also 10 g/L and 5 g/L, respectively. The expression level of IFN beta, as determined by SDS-PAGE, was 7.82% in the 12.5-h post-induction sample.

Example 8

Effect of Various Concentrations of Thiamine on Expression Level

The culture of *E. coli* BL21 (DE3) cells transformed with the IFN-beta gene was grown in Luria-Bertini medium (pH 7.0) with Ampicillin (100 mg/L) for 14 hours at 37° C. and 200 rpm in an incubator shaker. Subsequently the biomass was aseptically removed by centrifugation and re-suspended in the production medium. The composition of the production medium was as follows:

| Component | Concentration at the time of induction |
|---|---|
| Glucose | 5 g/L |
| Gelatin digest | 20 g/L |
| Thiamine | 0-12 g/L |
| Potassium cation | 90 mM |
| Ampicillin | 100 mg/L |

The IFN-β gene was subsequently induced by adding filter-sterilized IPTG (2 mM) at 37° C. The temperature during the production phase was kept at 37° C. Every two hours samples were taken and pH was adjusted to ~7.0. The IFN-β 1b expression level at 8-h post-induction samples was as shown in Table 2 below.

TABLE 2

| Thiamine Concentration (g/L) | IFN beta Expression Level (%) |
|---|---|
| 0 | 5.75 |
| 3 | 7.42 |
| 6 | 8.33 |
| 9 | 9.50 |
| 12 | 9.62 |

Example 9

Effect of Combination of Thiamine with Various Nitrogen Sources on Expression Level The culture of *E. coli* BL21 (DE3) cells transformed with the IFN-beta gene was grown in Luria-Bertini medium (pH 7.0) with Ampicillin (100 mg/L) for 14 hours at 37° C. and 200 rpm in an incubator shaker. Subsequently the biomass was aseptically removed by centrifugation and re-suspended in the production medium. The composition of the production medium was as follows:

| Component | Concentration at the time of induction |
|---|---|
| Glucose | 5 g/L |
| Nitrogen source | 20 g/L |
| Thiamine | 6-7 g/L |
| Potassium Cation | 90 mM |
| Ampicillin | 100 mg/L |

Figure 3:
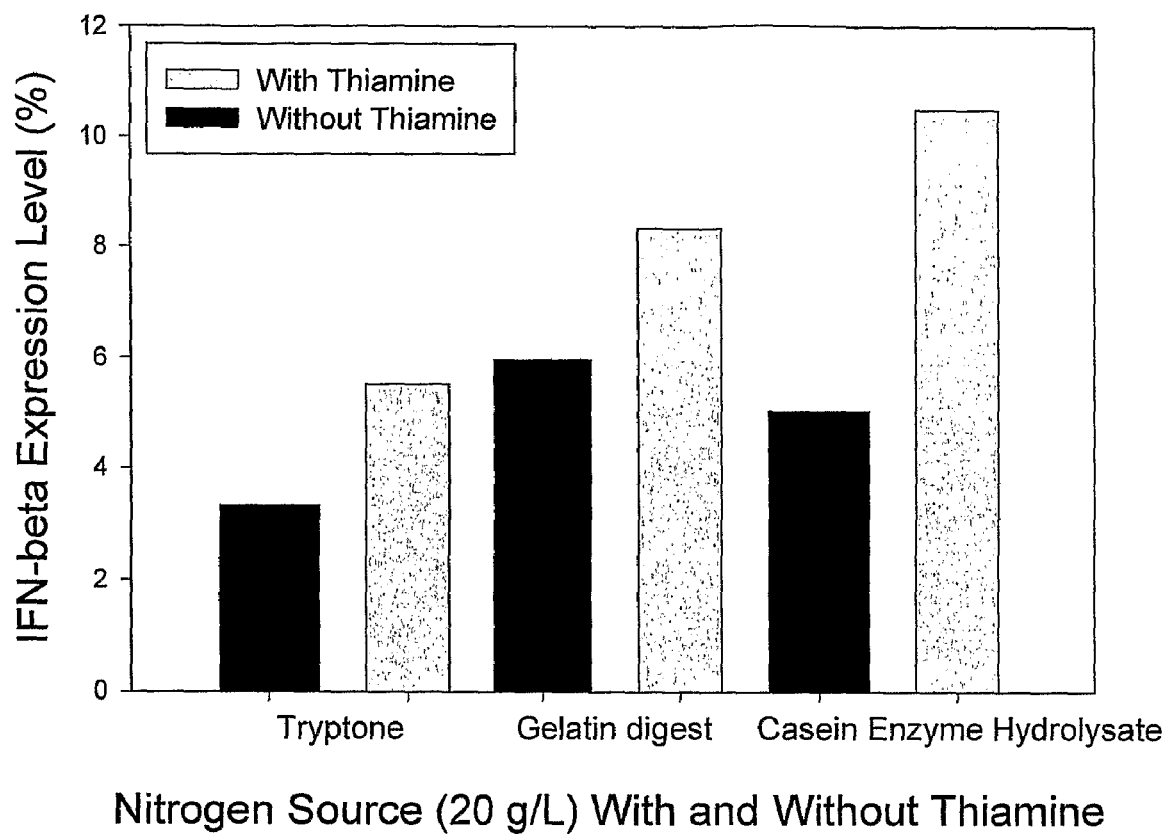
FIG. 3 shows the effect of Thiamine with various nitrogen sources and Potassium on IFN-β expression level. Experiments conducted in shake-flasks. Wherein the comparison of expression level was shown among Tryptone, Gelatin digest, and Casein Enzyme Hydrolysate, with Thiamine (Gray bars), and without Thiamine (Black bars) (6-7 g/L at the time of addition of inducer).

Effect of thiamine was monitored for three nitrogen sources i.e., gelatin digest, Casein Enzyme Hydrolysate and Tryptone. The IFN-β gene was subsequently induced by adding filter-sterilized IPTG (2 mM) at 37° C. The temperature during the production phase was kept at 37° C. Every two hours samples were taken and pH was adjusted to ~7.0. The IFN-β expression levels at 8-h post-induction samples (FIG. 3) are shown in Table 3 below.

TABLE 3

| Nitrogen Source | Thiamine Concentration (g/L) | IFN beta Expression Level (%) |
|---|---|---|
| Gelatin digest | 0 | 5.96 |
|  | 6 | 8.33 |
| Casein Enzyme Hydrolysate | 0 | 5.02 |
|  | 7 | 10.49 |
| Tryptone | 0 | 3.32 |
|  | 7 | 5.52 |

Example 10

Effect of Sodium Cation on Expression Level

The culture of *E coli* BL21 (DE3) cells transformed with the IFN-beta gene was grown in Luria-Bertini medium (pH 7.0) with Ampicillin (100 mg/L) for 14 hours at 37° C. and 200 rpm in an incubator shaker. Subsequently the biomass was aseptically removed by centrifugation at 7135×g for 15 minutes at 20° C. and aseptically re-suspended in the production medium. The composition of the media used for the production of IFN-β was as follows:

| Component | Concentration at the time of induction |
|---|---|
| Glucose | 5 g/L |
| Tryptone | 20 g/L |
| Thiamine | 7 g/L |
| Potassium Cation | 100 mM |
| Sodium cation | 60 mM, or <40 mM |
| Ampicillin | 100 mg/L |

The IFN-β gene was subsequently induced by adding filter-sterilized IPTG (2 mM) at 37° C.

The temperature during the production phase was kept at 37° C. and the pH in the range of 6.62-7.52. Every two hours samples were taken and pH was adjusted to ~7.0. The IFN beta expression level as measured densitometrically using protein bands with SDS-PAGE in 8-h post-induction samples, are shown in Table 4.

TABLE 4

| Sodium cation concentration | IFN beta Expression Level (%) |
|---|---|
| Medium containing 60 mM sodium | 7.15%. |
| Medium containing less than 40 mM sodium | 6.02% |

Example 11

Effect of Combination of Thiamine, High Sodium Cation Concentration and Tryptone on Expression Level A seed culture of *E. coli* BL21 (DE3) cells, transformed with the IFN-beta gene, was inoculated in the growth media of the following composition.

| Component | Concentration before inoculation |
|---|---|
| $KH_2PO_4$ | 13.3 g/L |
| $(NH_4)_2HPO_4$ | 4.0 g/L |
| Yeast extract | 1.0 g/L |
| Glucose | 10.0 g/L |
| Citric acid | 1.7 g/L |
| $MgSO_4 \cdot 7H_2O$ | 1.2 g/L |
| Trace element solution | 20.0 mL/L |
| Ampicillin | 100 mg/L |

Trace metal Solution:

| Component | Concentration |
|---|---|
| $FeCl_3 \cdot 6H_2O$ | 0.162 g/L |
| $ZnCl_2 \cdot 4H_2O$ | 0.0144 g/L |
| $CoCl_2 \cdot 6H_2O$ | 0.12 g/L |
| $Na_2MoO4 \cdot 2H_2O$ | 0.012 g/L |
| $CaCl_2 \cdot 2H_2O$ | 0.006 g/L |
| $CuCl_2$ | 1.9 g/L |
| $H_3BO_3$ | 0.5 g/L |

Adding the following media in substrate limited fed-batch mode brought about the major increase in biomass.

| Component | Concentration |
|---|---|
| Glucose | 700 g/L |
| $MgSO_4 \cdot 7H_2O$ | 20 g/L |
| Trace element solution | 20 mL/L |
| Ampicillin | 1.0 g/L |

In growth phase ammonium hydroxide was used as the pH regulator to maintain the pH in the range of 6.8 to 7.0. The temperature was maintained at 37° C. After achieving optical density of about 50 AU (at 600 nm), the pre-induction media was added.

Media A: Production without High Sodium Cation and Thiamine

Pre-Production Media:

| Component | Concentration in culture broth |
|---|---|
| Tryptone | 10 g/L |
| Thiamine | 1 g/L |
| Potassium | 90 mM final concentration in the broth |
| Sodium | No addition of Sodium salt |

The expression of IFN-beta gene was induced by aseptically adding filter-sterilized IPTG (2 mM).

Production Feed Media:

| Component | Concentration |
|---|---|
| Glucose | 270 g/L |
| Tryptone | 20 g/L |
| Thiamine | 7 g/L |
| $MgSO_4 \cdot 7H_2O$ | 1 g/L |
| Potassium | 90 mM |
| Sodium | No addition of Sodium salt |
| Ampicillin | 1 g/L |

In production phase ammonium hydroxide was used as the pH regulator to maintain the pH 7.0. The temperature was maintained at 37° C.

Media B: Production with High Sodium Cation and Thiamine

Pre-Production Media:

| Component | Concentration in culture broth |
|---|---|
| Tryptone | 10 g/L |
| Thiamine | 1 g/L |
| Potassium | 90 mM final concentration in the broth |
| Sodium | 60 mM final concentration in the broth |

The expression of IFN-beta gene was induced by aseptically adding filter-sterilized IPTG (2 mM).

Production Feed Media:

| Component | Concentration |
|---|---|
| Glucose | 270 g/L |
| Tryptone | 20 g/L |
| Thiamine | 7 g/L |
| $MgSO_4 \cdot 7H_2O$ | 1 g/L |
| Potassium | 90 mM |
| Sodium | 60 mM |
| Ampicillin | 1 g/L |

In production phase ammonium hydroxide was used as the pH regulator to maintain the pH 7.0. The temperature was maintained at 37° C. The total Sodium and Potassium cation concentration in the cell-free media, during the production phase was, 109-101±10.9-10.1 mM and 163-118±16.3-11.8 mM, respectively. The measurements of Potassium and Sodium cations in the cell-free culture broth were done using atomic absorption spectra.

Figure 4:
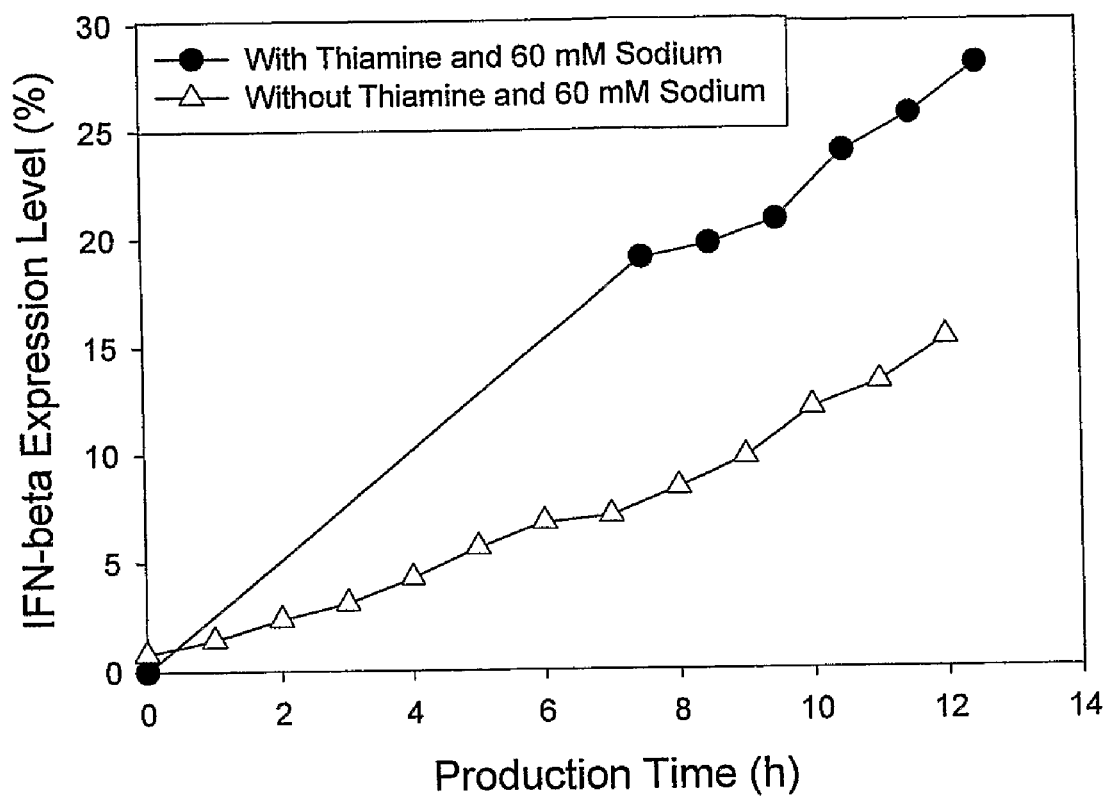
FIG. 4 shows the effect of a combination of Tryptone with Thiamine and high concentration of Sodium cation on IFN-β expression level. Experiments conducted in fermentors, when the comparison of expression levels was shown between a culture medium comprising of Thiamine and high Sodium cation (60 mM) (•), and with a culture medium without Thiamine and high Sodium cation (Δ).

The time course of increase in expression levels is shown in FIG. 4. The IFN beta expression levels obtained in media A and B were 15.24% and 27.32%, respectively, as measured densitometrically using protein bands obtained with SDS-PAGE. The IFN beta yield in media B was around 2 g/L.

Advantages of the Process:

1. The process of the present invention gives higher expression of IFN-beta than the prior art processes.

2. The process of the present invention is commercially more viable since there is no need to strictly monitor the sodium or potassium concentration in the medium to maintain it at a very low level.

3. The process of the present invention is easier to perform than the prior art processes.

4. The overall process of the present invention is very cost effective.

We claim:

1. A process for the production of interferon beta in an *Escherichia coli* host cell comprising the steps of:
   a) providing the host cell that is capable of producing the said protein; and
   b) culturing the cell under conditions effective to induce production of the protein in a medium comprising a complex nitrogen source selected from gelatin digest, casein enzyme hydrolysate, and tryptone, either alone or in a mixture thereof, or any of said medium in combination with yeast extract, where the process is carried out at a pH at about 6.5 to 7.0 and at a temperature about 37° C.; and
   c) wherein the culture media further comprises thiamine at a concentration of at least 3 g/L.

2. The process as claimed in claim 1, wherein the concentration of the complex nitrogen source varies between about 10 to about 30 g/L.

3. The process as claimed in claim 1, wherein the complex nitrogen source is gelatin digest.

4. The process as claimed in claim 1, wherein the complex nitrogen source is tryptone.

5. The process as claimed in claim 1, wherein the complex nitrogen source is casein enzyme hydrolysate.

6. The process as claimed in claim 1, wherein the media further comprises thiamine at a concentration of at least 3 to 12 g/L.

7. The process according to claim 6, wherein the concentration of thiamine is 7 g/L.

8. The process as claimed in claim 1, wherein said medium further comprises a carbon source selected from the group comprising glucose, fructose, maltose, glycerol, galactose and a combination thereof.

9. The process as claimed in claim 1, wherein the carbon source is selected from glucose or glycerol.

10. The process as claimed in claim 1 wherein said medium comprises about 50-100 mM sodium cation concentration.

11. The process as claimed in claim 1, wherein the interferon beta comprises the amino acid sequence of SEQ ID NO:1.

12. The process as claimed in claim 1, wherein the interferon beta expression level at the end of production is at least 15% of the total protein.

13. A composition for producing interferon beta, comprising:
   a) an *E. coli* cell capable of producing interferon beta, and
   b) a culture medium comprising a complex nitrogen source selected from a group comprising tryptone, casein enzyme hydrolysate and gelatin digest, a carbon source selected from a group comprising glucose and glycerol; thiamine at a concentration of at least 3 g/L and sodium cation in the range of 60-80 mM.

* * * * *